(12) United States Patent
Kim et al.

(10) Patent No.: US 11,268,114 B2
(45) Date of Patent: Mar. 8, 2022

(54) METHOD FOR PRODUCING ANHYDROUS GALACTOSE DERIVED FROM SEAWEED

(71) Applicant: Korea University Research and Business Foundation, Seoul (KR)

(72) Inventors: Kyoung Heon Kim, Seoul (KR); Sang-Hyun Lee, Daejeon (KR); Dong-Hyun Kim, Busan (KR); Eun-Ju Yun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 16/467,129

(22) PCT Filed: Nov. 24, 2017

(86) PCT No.: PCT/KR2017/013493
§ 371 (c)(1),
(2) Date: Jun. 6, 2019

(87) PCT Pub. No.: WO2018/105932
PCT Pub. Date: Jun. 14, 2018

(65) Prior Publication Data
US 2020/0071737 A1    Mar. 5, 2020

(30) Foreign Application Priority Data
Dec. 7, 2016 (KR) .................. 10-2016-0165598

(51) Int. Cl.
*C12P 19/14* (2006.01)
*C07H 3/04* (2006.01)
*C12P 19/02* (2006.01)

(52) U.S. Cl.
CPC ............... *C12P 19/14* (2013.01); *C07H 3/04* (2013.01); *C12P 19/02* (2013.01)

(58) Field of Classification Search
CPC ........... C12P 19/14; C12P 19/02; C12P 19/12; C07H 3/04; C12N 9/2402
See application file for complete search history.

(56) References Cited

U.S. PATENT DOCUMENTS

2015/0216778 A1  8/2015  Kim et al.
2016/0265012 A1  9/2016  Kim et al.

FOREIGN PATENT DOCUMENTS

KR  10-2011-0072958 A  6/2011
KR  10-2013-0085017 A  7/2013
KR  10-2015-0043040 A  4/2015

OTHER PUBLICATIONS

Weiner et al. Complete Genome Sequence of the Complex Carbohydrate-Degrading Marine Bacterium, Saccharophagus degradans Strain 2-40.PLoS (2008), 4(5): p. 1-13.*
Yun et al. Production of 3,6-anhydro-l-galactose from agarose by agarolytic enzymes of Saccharophagus degradans 2-40. Process Biochemistry (2011), 46:88-93.*
Tanaka et al. Ethanol Production from Starch by a Coimmobilized Mixed Culture System of Aspergillus awamori and Zymomonas mobilis. Biotechnology and Bioengineering, vol. XXVIII, pp. 1761-1768 (1986).*
Kyoung Heon Kim, "Enzyme-based Red Algae Sugar Platform for the Production of Industrial Chemicals and Fuels," Key Joint Research Program Final Report, Ministry of Science and ICT, May 2014, pp. 1-71 (73 pages).
NCBI, GenPept accession No. WP_011467876.1, Feb. 6, 2016, 2 pages.
International Search Report of PCT/KR2017/013493 dated Feb. 19, 2018.

* cited by examiner

*Primary Examiner* — Iqbal H Chowdhury
(74) *Attorney, Agent, or Firm* — Sughrue Mion, PLLC (57) ABSTRACT

The present invention relates to a method for producing anhydrous galactose derived from seaweed, and provides an improved production yield rate of 3,6-anhydro-L-galactose by using microorganisms during acid treatment, neutralization, and purification after enzymatic hydrolysis, of agarose or agar.

4 Claims, 10 Drawing Sheets

Specification includes a Sequence Listing.

METHOD FOR PRODUCING ANHYDROUS GALACTOSE DERIVED FROM SEAWEED

CROSS REFERENCE TO RELATED APPLICATIONS

This application is a National Stage of International Application No. PCT/KR2017/013493, filed on Nov. 24, 2017, which claims priority from Korean Patent Application No. 10-2016-0165598, filed on Dec. 7, 2016.

BACKGROUND

1. Field of the Invention

The present invention relates to a method of producing anhydrous galactose derived from seaweed, in which the production yield of 3,6-anhydro-L-galactose is enhanced using a microorganism in a purification process after acid treatment, neutralization, and enzymatic hydrolysis of agarose or agar.

2. Discussion of Related Art

A major polysaccharide constituting red algae is agarose, and agarose is a polymer in which 3,6-anhydro-L-galactose (hereinafter, referred to as "AHG") and D-galactose are alternately bound via α-1,3 linkage and β-1,4 linkage. Among these, AHG is a multifunctional high-value-added material having an anticariogenic function and a colorectal cancer prevention function as well as cosmetic whitening and moisturizing functions. Therefore, it is very important to efficiently produce AHG from agar or agarose, which is the main carbohydrate of red algae, and efficiently purify AHG.

Methods of producing AHG are as follows. First, there is a method of producing AHG by hydrolyzing agarose or agar using a strong acid at a high temperature. This method is inexpensive and simple, but disadvantageous in that AHG and D-galactose, which are monosaccharides, are decomposed into 5-hydroxymethyl furfural (5-HMF) at high temperatures, resulting in a reduced AHG production yield. Second, there is a method of producing AHG by hydrolyzing agarose or agar using an enzyme at room temperature. However, this method is not capable of allowing a high concentration reaction due to low solubility of agarose or agar, and thus the concentration of produced AHG is very low and accordingly, separation and purification costs increase, resulting in a reduced AHG production yield. Third, agarose or agar is decomposed into agarooligosaccharides (AOSs) using a weak acid such as acetic acid, and then the AOSs are produced as neoagarobiose (NAB) through an enzymatic reaction of exo-type β-agarase II. However, in this case, agarotriose is produced as a by-product, and it is necessary to introduce an additional enzyme called agarolytic β-galactosidase (ABG) in order to decompose the agarotriose. Subsequently, AHG and D-galactose, which are monosaccharides, may be obtained through an enzymatic reaction of neoagarobiose hydrolase (NABH). However, when acetic acid is used in a pretreatment reaction, which is the first step of this process, a large amount of salt is produced in the subsequent neutralization process. In addition, since a recombinant enzyme must be produced through fermentation separately in order to produce an enzyme for the reaction, the process is very complicated and production costs increase, resulting in reduced economic efficiency. Fourth, there is a pretreatment method using a low concentration of a neutral buffer at a high temperature (170° C.), but this method requires a high-temperature and high-pressure reactor in mass production. In addition, AHG is over-decomposed into 5-HMF during the pretreatment process, thus reducing AHG production yield.

SUMMARY OF THE INVENTION

An object of the present invention is to provide a method of producing agarobiose from agarose or agar through strong acid treatment and neutralization.

Another object of the present invention is to provide a method of producing 3,6-anhydro-L-galactose through anaerobic and aerobic culturing of a microorganism with agarose or agar having undergone strong acid treatment, neutralization, and enzymatic hydrolysis.

To achieve the aforementioned objects, the present invention provides a method of producing agarobiose, including allowing agarose or agar used as a substrate in an amount of 10% (w/v) to 37% (w/v) with respect to a dry weight to react with a strong acid at a concentration of 0.1% (w/v) to 5% (w/v) at 80° C. to 140° C. for 5 minutes to 500 minutes and performing neutralization to obtain a reaction product including agarobiose, in which a yield of 5-hydroxymethyl furfural in the reaction product is less than 1.5% (w/w).

The present invention also provides a method of producing 3,6-anhydro-L-galactose, including: a step of allowing agarose or agar used as a substrate in an amount of 10% (w/v) to 37% (w/v) with respect to a dry weight to react with a strong acid at a concentration of 0.1% (w/v) to 5% (w/v) at 80° C. to 140° C. for 5 minutes to 500 minutes and performing neutralization to obtain a reaction product including agarobiose, wherein a yield of 5-hydroxymethyl furfural in the reaction product is less than 1.5% (w/w);

a step of allowing the reaction product to react with agarooligosaccharide hydrolase, which uses agarobiose as a substrate; and a step of culturing a microorganism having the ability to metabolize galactose in the presence of the hydrolysate obtained by the above step and obtaining 3,6-anhydro-L-galactose from the resulting microorganism culture broth.

According to the present invention, AHG is obtained without a separate existing purification process through established optimum conditions capable of producing a high concentration of agarobiose by treatment of agarose or agar with a strong acid and neutralization thereof, and through culturing of an enzyme using agarobiose as a substrate and a microorganism using galactose as a substrate, and thus AHG loss can be reduced, thus providing an effect of obtaining AHG with a high yield.

BRIEF DESCRIPTION OF THE DRAWINGS

A of FIG. 2 is a graph showing the degree of liquefaction obtained after agarose was treated with a 0.5% (w/v) strong acid, followed by acid hydrolysis at 140° C. for 10 minutes according to the AHG production process of the present invention, and B of FIG. 2 illustrates TLC analysis results of the reaction product.

DETAILED DESCRIPTION OF EXEMPLARY EMBODIMENTS

Hereinafter, the configuration of the present invention will be described in detail.

The present invention relates to a method of producing agarobiose, including: allowing agarose or agar used as a substrate in an amount of 10% (w/v) to 37% (w/v) with respect to a dry weight to react with a strong acid at a concentration of 0.1% (w/v) to 5% (w/v) at 80 r to 140 r for 5 minutes to 500 minutes and performing neutralization to obtain a reaction product including agarobiose, in which a yield of 5-hydroxymethyl furfural in the reaction product is less than 1.5% (w/w).

The present invention also provides a method of producing 3,6-anhydro-L-galactose, including: a step of allowing agarose or agar used as a substrate in an amount of 10% (w/v) to 37% (w/v) with respect to a dry weight to react with phosphoric acid at a concentration of 0.1% (w/v) to 5% (w/v) at 80° C. to 140° C. for 5 minutes to 500 minutes and performing neutralization to obtain a reaction product including agarobiose, wherein a yield of 5-hydroxymethyl furfural in the reaction product is less than 1.5% (w/w);

a step of allowing the reaction product to react with agarooligosaccharide hydrolase, which uses agarobiose as a substrate; and a step of culturing a microorganism having the ability to metabolize galactose in the presence of the hydrolysate obtained by the above step and obtaining 3,6-anhydro-L-galactose from the resulting microorganism culture broth.

Figure 1:
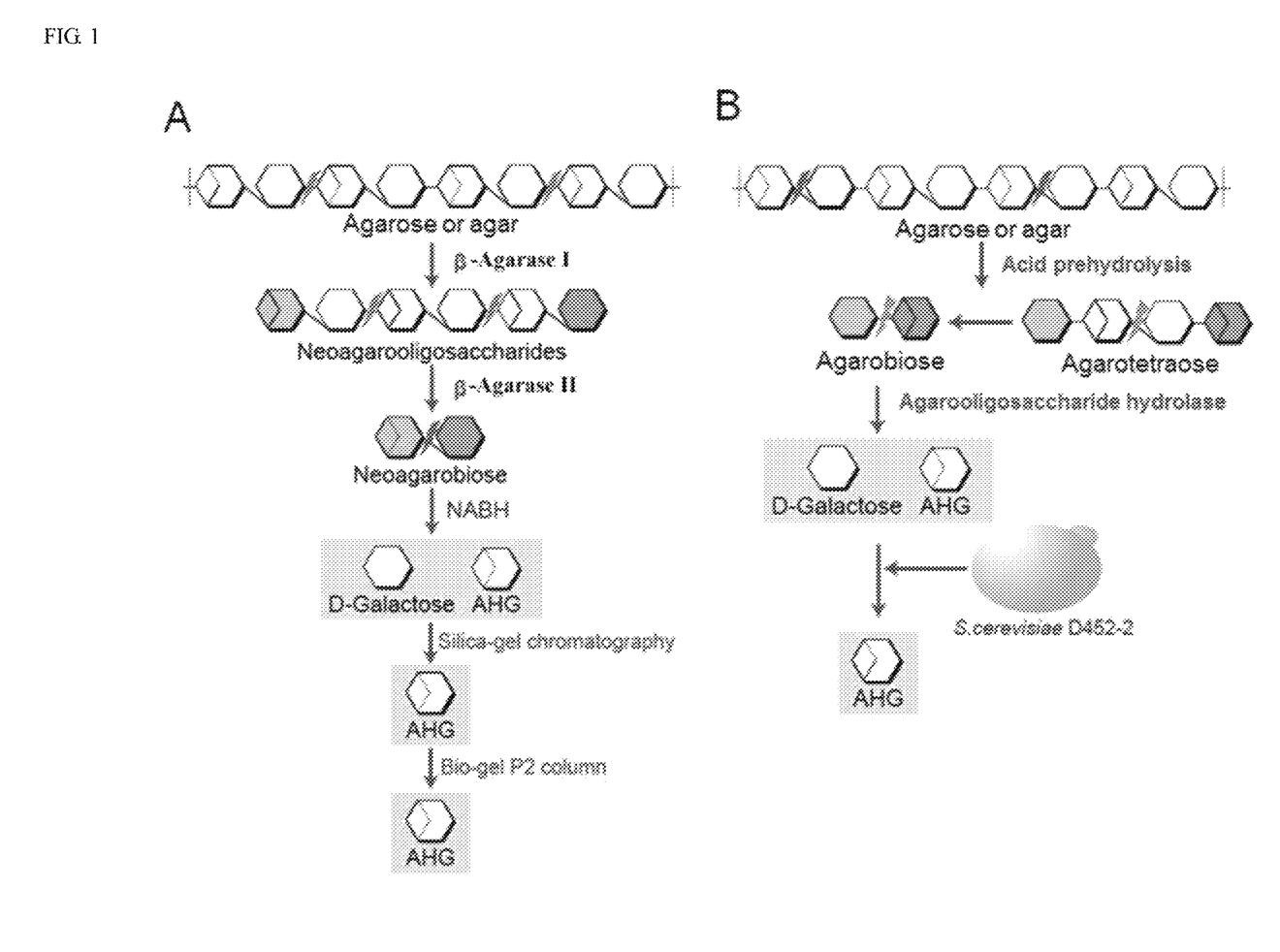
FIG. 1 is a schematic diagram illustrating production of AHG from agarose or agar and purification thereof, wherein A diagram inserted within the FIG. 1 illustrates a process of producing AHG through conventional enzyme saccharification and purifying AHG using a microorganism, and B diagram inserted within the FIG. 1 illustrates an AHG production process of the present invention.

To address problems found in conventionally known AHG production methods, first, the inventors of the present invention established a condition of minimum production of 5-HMF even when a strong acid was used for the production of AHG and performed a pretreatment reaction on agarose or agar at a high concentration, thereby obtaining agarooligosaccharides, particularly agarobiose with a high yield at a high concentration (see FIG. 1). Second, the agarobiose and agarooligosaccharides obtained with a high yield at a high concentration is neutralized with a strong base, and at this time, salt produced through neutralization (e.g., phosphate) is not removed and used as a buffer solution in the next step, i.e., the agarooligosaccharide hydrolase reaction. Third, AHG and D-galactose are produced at high concentrations using agarooligosaccharide hydrolase, which efficiently degrades agarobiose. Fourth, AHG is purified using yeast, which is generally recognized as a safe (GRAS) microorganism for humans. Under anaerobic or aerobic conditions, AHG and D-galactose, which are enzyme reaction products, are supplied as carbon sources during yeast culture, and among these, only galactose may be selectively metabolized to thereby purify AHG (see B of FIG. 1). This purification method does not use an organic solvent harmful to the human body, and since the amount of AHG lost during the purification process is almost none, the purified AHG may be obtained with a high yield.

The concentration of the strong acid used in the strong acid treatment of agarose or agar may range from 0.1% (w/v) to 5% (w/v), more particularly 0.5% (w/v) to 3% (w/v). When the concentration of the strong acid is within the above range, the production of 5-HMF by strong acid treatment of agarose or agar may be minimized, and at the same time, a high concentration of agarobiose may be produced, and thus the production of AHG with a high yield is possible.

The treatment of agarose or agar with a strong acid may be a reaction of agarose or agar with a 0.1% (w/v) to 5% (w/v) strong acid at 80° C. to 140° C. for 5 minutes to 500 minutes. More particularly, the treatment may be a reaction of agarose as a substrate with a 0.5% (w/v) to 2% (w/v) strong acid at 100° C. to 140° C. for 5 minutes to 20 minutes. More particularly, the treatment may be a reaction of agar as a substrate with a 1% (w/v) to 3% (w/v) strong acid at 80° C. to 100° C. for 60 minutes to 480 minutes.

The strong acid may be phosphoric acid, sulfuric acid, hydrochloric acid, nitric acid, or the like. More specifically, the strong acid may be phosphoric acid.

After the treatment of agarose or agar with a strong acid, agarooligosaccharides including a high concentration of agarobiose may be produced.

The amount of the agarose or agar used in the strong acid treatment may range from 10% (w/v) to 37% (w/v), more particularly 15% (w/v) to 31% (w/v), and more particularly 16.8% to 30.7% (w/w), with respect to a dry weight. When the amount of the agarose or agar is within the above range, a degree of liquefaction of 90%, 95%, or 98% may be obtained. When the amount of the agarose or agar is outside the above range, a substrate degradation rate may be significantly reduced.

The strong acid-treated agarose or agar is neutralized to a pH of 5 to 7 by adding a strong base thereto.

As the strong base, NaOH, KOH, $Ca(OH)_2$, $Ba(OH)_2$, or the like may be used, but the present invention is not limited thereto.

The agarooligosaccharide hydrolase is an enzyme that decomposes agarobiose as a substrate into D-galactose and 3,6-anhydro-L-galactose, and may include the amino acid sequences set forth in SEQ ID NO: 1.

The agarooligosaccharide hydrolase may be transcribed and translated through a DNA segment, i.e., a coding gene, involved in producing a polypeptide including an intervening sequence between individual coding segments as well as a region before and after the coding region of the enzyme. For example, the agarooligosaccharide hydrolase may be transcribed and translated from the sequences set forth in SEQ ID NO: 2, but is not particularly limited thereto. Also, as mutant proteins having one or more substitutions, deletions, dislocations, additions, or the like of the enzyme, proteins having an agarobiose hydrolytic activity are also within the scope of the enzyme of the present invention. Preferably, the agarooligosaccharide hydrolase includes an amino acid sequence with at least 80% homology, at least 85% homology, at least 90% homology, at least 93% homology, at least 94% homology, at least 95% homology, at least 96% homology, at least 97% homology, at least 98% homology, and at least 99% homology to the amino acid sequences set forth in SEQ ID NO: 1.

The agarooligosaccharide hydrolase may be derived from *Saccharophagus degradans* 2-40$^T$, but the present invention is not particularly limited thereto.

The agarooligosaccharide hydrolase may be separated and purified from a supernatant of a culture of *Saccharophagus degradans* 2-40$^T$, and may be produced and separated: from strains other than *Saccharophagus degradans* using a genetic recombination technique; or by an artificial chemical synthesis method or the like. When the recombination technique is used, a culture supernatant or a supernatant of *Saccharophagus degradans* may be used instead of the agarooligosaccharide hydrolase, but the present invention is not particularly limited thereto. According to one embodiment, the agarooligosaccharide hydrolase may be obtained from *E. coli* transformed with a recombinant vector including the base sequences set forth in SEQ ID NO: 2 or a culture broth thereof.

A reaction between the agarobiose and the agarooligosaccharide hydrolase may be performed at a temperature of 20° C. to 40° C. and 100 rpm to 300 rpm for 5 hours to 48 hours. More particularly, the reaction therebetween may be performed at a temperature of 30° C. to 40° C. for 10 hours to 24 hours.

In the present specification, the terms "protein" and "polypeptide" may be used interchangeably.

In the present invention, a polypeptide having a sequence homology of a certain percentage (for example, 80%, 85%, 90%, 95%, or 99%) with respect to another sequence means that two sequences has the same amino acid residues at the above percentage upon sequence comparison when the two sequences are aligned. The alignment and percentage homology or identity may be determined using any suitable software program known in the related art, for example, those described in Current Protocols in Molecular Biology (F. M. Ausubel, et al., (eds) 1987 Supplement 30 section 7.7.18). A preferred program includes the GCG Pileup program, FASTA (Pearson, et al., 1988 *Proc. Natl. Acad. Sci. USA* 85: 2444-2448), and BLAST (BLAST Manual, Altschul et al., Natl. Cent. Biotechnol. Inf., Natl Lib. Med. (NCIB NLM NIH), Bethesda, Md., and Altschul et al., 1997 NAR 25: 3389-3402). Another preferred alignment program is ALIGN Plus (Scientific and Educational Software, PA), which preferably uses basic parameters. Still another preferred sequence software program which may be used herein is a TFASTA Data Searching program available in Sequence Software Package Version 6.0 (Genetics Computer Group, University of Wisconsin, Madison Wis.).

In the present invention, the term "recombination" used in connection with cells, nucleic acids, proteins, or vectors indicates that the cells, nucleic acids, proteins, or vectors are modified by introduction of heterologous nucleic acids or proteins or alteration of inherent nucleic acids or proteins, or that the cells are derived from such modified cells. That is, the recombinant cells, for example, express genes which are not found in the cells in an inherent (non-recombinant) form, or express inherent genes which are expressed abnormally upon expression or not expressed at all.

In this specification, the term "nucleic acid" encompasses all types of single- or double-stranded DNAs, RNAs, and chemical variants thereof. The terms "nucleic acid" and "polynucleotide" may be used interchangeably herein. Since the genetic codes are degenerate, one or more codons may be used to encode a specific amino acid, and the present invention encompasses polynucleotides encoding certain amino acid sequences.

The term "introduction" used to describe an insertion of a nucleic acid sequence into cells refers to "transfection," "transformation," or "transduction," and encompasses references to the integration of a nucleic acid sequence into eukaryotic or prokaryotic cells. In this case, the nucleic acid sequence is integrated into the genome (for example, a chromosome, a plasmid, a plastid, or mitochondrial DNA) of a cell, and converted into an autonomous replicon or expressed temporarily.

In the method of producing 3,6-anhydro-L-galactose of the present invention, agarobiose is hydrolyzed into D-galactose and AHG by the agarooligosaccharide hydrolase, which uses agarobiose as a substrate, and when a microorganism having the ability to metabolize galactose is cultured therewith under anaerobic or aerobic conditions, galactose is consumed in the microorganism culture broth, and only AHG remains. Therefore, there is no need to go through an additional process of separately purifying AHG from a hydrolysate including galactose and AHG.

The microorganism having the ability to metabolize galactose may be any one of: lactic acid bacteria including *Bifidobacterium* and *Lactobacillus* such as *L. casei, L. acidophilus, L. bulgaricus, B. longum, B. bifidum, Actiregularis*, and the like; *Bacillus; Streptomyces; Corynebacterium; Zymomonas* such as *Z. mobilis* and the like; *Escherichia coli*; and yeasts such as *Saccharomyces cerevisiae, P. pastoris*, and the like. These are the aforementioned harmless GRAS microorganisms which metabolize galactose, and thus only a microorganism and AHG remain in a microorganism culture broth.

Therefore, a microorganism or cell debris is removed by centrifugation or filtration of the microorganism culture broth without the conventional purification process, and AHG remains in the remaining liquid, so that AHG can be obtained with a high yield.

The microorganism having the ability to metabolize galactose may be cultured under aerobic or anaerobic conditions. More preferably, the microorganism may be cultured under anaerobic conditions, and anaerobic culturing conditions such as culture medium, culture temperature, time, and the like can be performed within the range of understanding of those skilled in the art, and the present invention is not particularly limited thereto.

Hereinafter, the present invention will be described in more detail with reference to examples according to the present invention, but these examples are not intended to limit the scope of the present invention.

EXAMPLES

Example 1

Establishment of Acid Hydrolysis Conditions

When agarose or agar is hydrolyzed with a strong acid, AHG or D-galactose is over-decomposed and converted to 5-HMF. Therefore, acid hydrolysis was performed in a microwave digestion system using dilute phosphoric acid obtained by diluting phosphoric acid.

To examine the hydrolytic effect of dilute phosphoric acid, first, the amount of substrate added was optimized. 16.8% (w/v), 23.8% (w/v), 30.7% (w/v), or 36.8% (w/v) of an agarose substrate was subjected to acid hydrolysis using 0.5% (w/v) phosphoric acid at 140° C. for 10 minutes. At this time, the amount of used agarose is based on a dry weight. The degree of liquefaction was expressed as a percentage of a value obtained by subtracting, from an initial weight (g) of agarose added, the amount (g) of precipitate dried at 105° C. for 12 hours after having undergone acid hydrolysis and centrifugation at 12,000×g and 4° C. for 30 minutes, and dividing the resulting value by the initial weight of agarose added.

Figure 2:
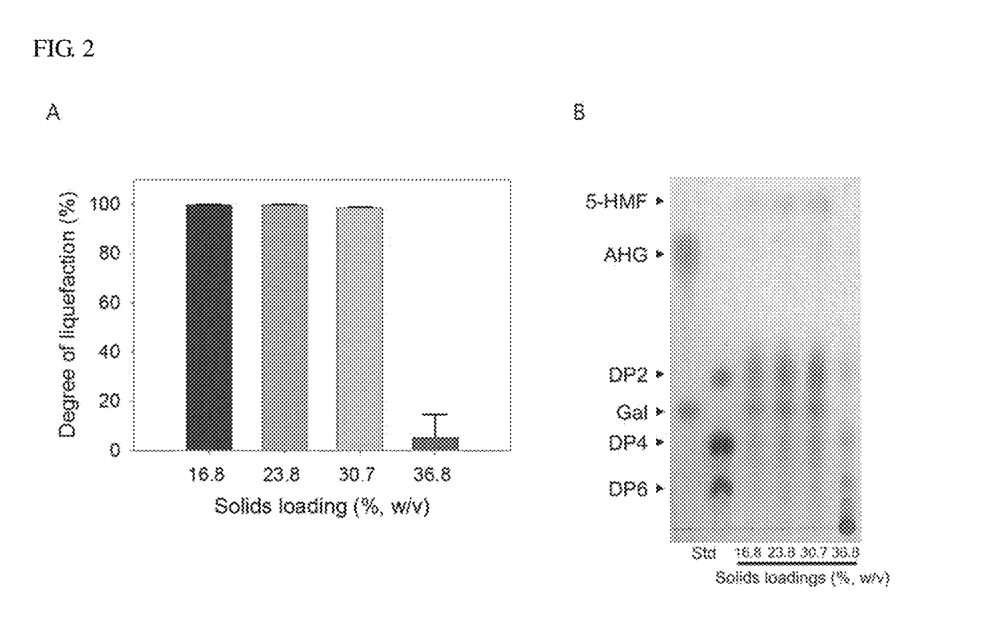

As a result, as shown in A of FIG. 2, when the substrate was added in an amount of 16.8% to 30.7%, a degree of liquefaction of 98% or higher was obtained, whereas the degree of liquefaction under a condition of adding 36.8% of the substrate was significantly reduced, i.e., 5%. From this result, it was confirmed that, as illustrated in B of FIG. 2, which illustrates TLC measurement results, agarose was not adequately degraded under a condition of adding 36.8% of the substrate. In the production process, it is very important to add a high concentration of substrate since AHG, which is a final product, can be produced at a concentration as high as possible. In addition, the consumption of water and energy and the size of a reactor may be reduced, and thus production costs may be lowered. Thus, a subsequent acid hydrolysis condition was established by selecting 30.7%, which is the largest amount of substrate added.

To produce agarooligosaccharides, especially agarobiose, which is effective for use in acid hydrolysis, hydrolysis was performed with 0.5% (w/v), 1% (w/v), or 2% (w/v) phosphoric acid at a reaction temperature of 110° C., 120° C., 130° C., or 140° C. for 5 minutes or 10 minutes.

Table 1 shows results of confirming the degree of liquefaction and the yields of agarobiose and 5-HMF in accordance with hydrolysis conditions.

TABLE 1

| Acid pretreatment conditions | | Degree of liquefaction (%, w/w) | Agarobiose yield (%, w/w) | 5-HMF yield (%, w/w) |
|---|---|---|---|---|
| Phosphoric acid 0.5% (w/v) | 120° C., 10 min | 18.5 ± 6.3 | 4.0 ± 0.1 | 0.0 ± 0.0 |
| | 130° C., 5 min | 91.1 ± 7.0 | 19.5 ± 5.2 | 0.2 ± 0.1 |
| | 130° C., 10 min | 99.3 ± 0.1 | 44.7 ± 0.9 | 0.9 ± 0.0 |
| | 140° C., 5 min | 99.0 ± 1.3 | 21.8 ± 5.1 | 0.2 ± 0.1 |
| | 140° C., 10 min | 99.2 ± 0.1 | 57.2 ± 0.2 | 4.2 ± 0.3 |
| Phosphoric acid 1% (w/v) | 110° C., 5 min | 64.4 ± 9.7 | 10.5 ± 1.7 | 0.0 ± 0.0 |
| | 110° C., 10 min | 99.4 ± 0.2 | 39.0 ± 1.4 | 0.2 ± 0.0 |
| | 120° C., 5 min | 93.8 ± 0.7 | 24.3 ± 5.1 | 0.1 ± 0.0 |
| | 120° C., 10 min | 99.7 ± 0.2 | 59.1 ± 3.7 | 0.5 ± 0.1 |
| | 130° C., 5 min | 99.9 ± 0.4 | 66.1 ± 1.1 | 1.2 ± 0.3 |
| | 130° C., 10 min | 99.2 ± 0.1 | 49.3 ± 10.4 | 7.3 ± 3.3 |
| | 140° C., 5 min | 99.4 ± 0.1 | 62.5 ± 1.1 | 2.9 ± 0.6 |
| | 140° C., 10 min | 98.4 ± 0.2 | 32.4 ± 0.8 | 11.1 ± 2.2 |
| Phosphoric acid 2% (w/v) | 110° C., 5 min | 99.6 ± 0.2 | 47.2 ± 7.1 | 0.2 ± 0.1 |
| | 110° C., 10 min | 99.4 ± 0.3 | 70.0 ± 1.2 | 1.3 ± 0.6 |
| | 120° C., 5 min | 99.3 ± 0.1 | 67.0 ± 2.6 | 0.8 ± 0.4 |
| | 120° C., 10 min | 99.3 ± 0.1 | 64.4 ± 3.9 | 2.5 ± 1.3 |
| | 130° C., 5 min | 99.3 ± 0.2 | 65.4 ± 2.1 | 2.1 ± 0.5 |
| | 130° C., 10 min | 99.2 ± 0.2 | 44.6 ± 6.8 | 9.0 ± 2.3 |
| | 140° C., 5 min | 99.5 ± 0.1 | 53.1 ± 6.9 | 5.7 ± 1.4 |
| | 140° C., 10 min | 98.9 ± 0.1 | 25.2 ± 3.0 | 16.9 ± 1.9 |

As shown in Table 1, a degree of liquefaction of 18.5% to 93.8% was exhibited under conditions of 0.5% phosphoric acid, 120° C., 10 min, and 130° C., 5 min and under conditions of 1% phosphoric acid, 110° C., 5 min, and 120° C., 5 min, from which it was confirmed that agarose was unable to be completely hydrolyzed. However, as acid concentration and temperature increased, the monosaccharide was over-decomposed, and thus 5-HMF yield was also increased. In contrast, as acid concentration, temperature, and reaction time increased, the degree of liquefaction was increased and agarobiose yield was also increased.

To analyze the types of reaction products in accordance with the above conditions, TLC, GC/TOF-MS, and HPLC analyses were performed.

For TLC, 1 µl of an enzyme reaction product was loaded onto a silica gel plate and developed on a mobile phase consisting of a mixture of n-butanol, ethanol, and water in a volume ratio (v/v/v) of 3:1:1 for 2 hours, followed by color development using 10% sulfuric acid and 0.2% 1,3-dihydroxynaphthalene.

A derivatization process for GC/TOF-MS analysis is as follows. The pretreatment reaction product was centrifuged at 16,000×g for 5 minutes, and then 20 µl of the supernatant was dried with a speed bag. 10 μl of 4% (w/v) O-methylhydroxylamine hydrochloride in pyridine was added to the sample dried for derivatization and a reaction was allowed to occur therebetween at 30° C. for 90 minutes and then 45 μl of N-methyl-N-(trimethylsilyl)trifluoroacetamide was added thereto and a reaction was allowed to occur therebetween at 37° C. for 30 minutes. Device conditions for the analysis are as follows. A column used for the analysis was RTX-5Sil MS (30 m×0.25 mm i.d., 25 μm film thickness, Resteck), the column temperature was first maintained at 50° C. for 1 minute and raised to 330° C. at a heating rate of 20° C./min, and then the temperature was maintained at 330° C. for 5 minutes. 1 μl of each sample was analyzed at a split ratio of 5.

For the HPLC analysis, each sample was analyzed using a KS-802 column (Shodex) at a column temperature of 80° C. and a flow rate of 0.5 mL/min. At this time, water was used as a mobile phase.

Figure 3A:
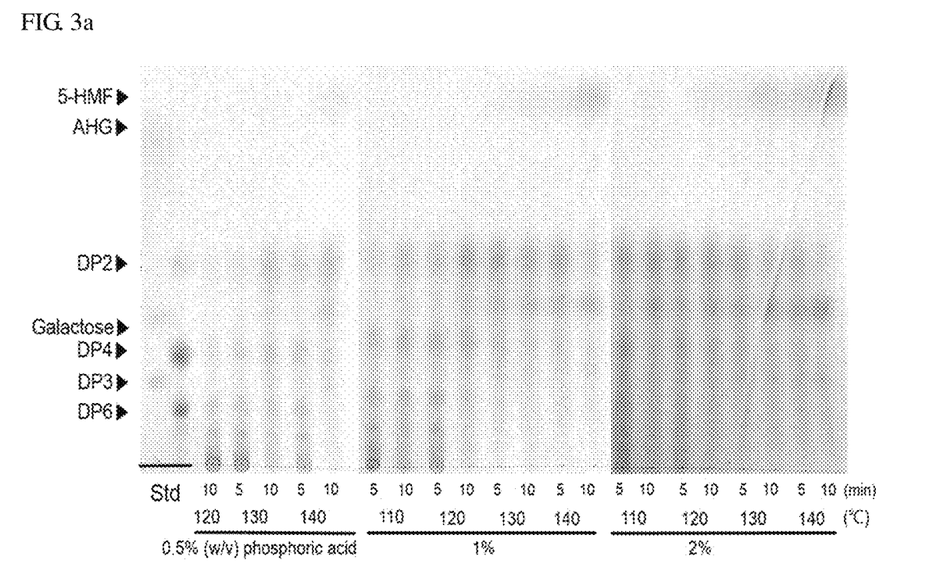
FIG. 3a illustrates TLC analysis results of a reaction product obtained by treating agarose with 0.5% (w/v), 1% (w/v), or 2% (w/v) phosphoric acid, followed by acid hydrolysis at 110° C. for 10 minutes according to the AHG production process of the present invention.
Figure 3B:
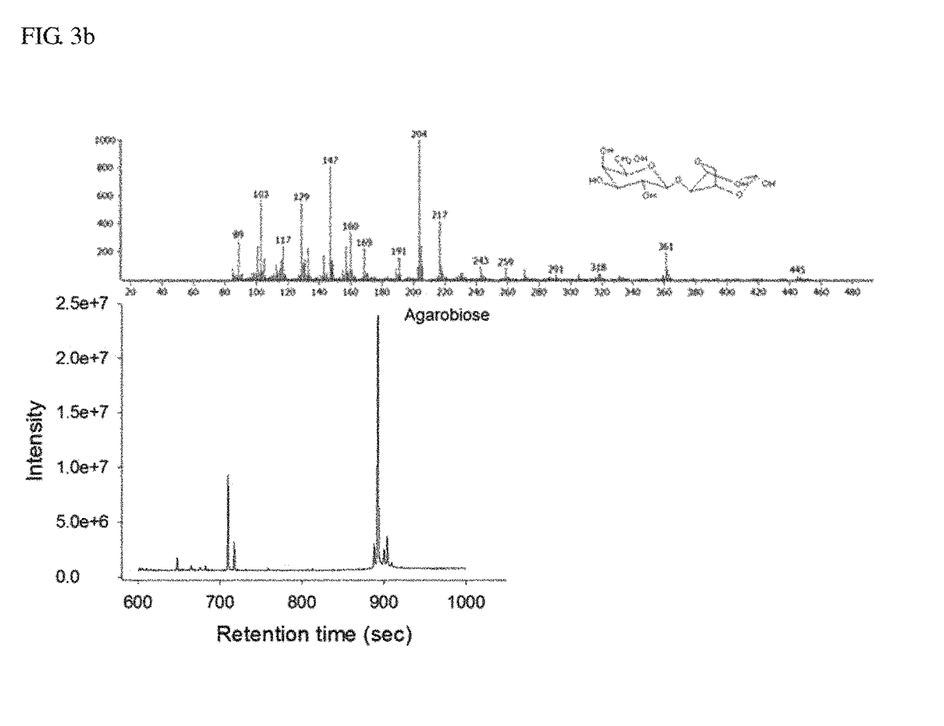
FIG. 3b illustrates GC-TOF/MS analysis results of a reaction product obtained by treating agarose with 2% (w/v) phosphoric acid, followed by acid hydrolysis at 110° C. for 10 minutes according to the AHG production process of the present invention.

As shown in FIG. 3a and Table 1, it was confirmed that, while a higher degree of polymerization (DP) was exhibited under a condition of a lower concentration of phosphoric acid, agarobiose having a DP of 2 was mainly produced as acid concentration increased. Among the above conditions, under conditions of 1% phosphoric acid and 130° C., 5 min and conditions of 2% phosphoric acid, 110° C., 10 min, and 120° C., 5 min, the agarobiose yield was highest, i.e., 66.1%, 67.0%, and 70.0% for the respective conditions (see FIG. 3b), and under these conditions, the 5-HMF yield was low, i.e., 1.2%.

Example 2

Cloning, Expression, and Purification of Agarooligosaccharide Hydrolase

A gene encoding β-agarooligosaccharide hydrolase was obtained through PCR using *Saccharophagus degradans* 2-40$^T$ (ATCC 43961) as a template and the following primers:

```
Forward primer (SEQ ID NO: 3):
5'-ATACATATGAATAGACTTACACTACCGCCTTCTTCTCGT-3';

Reverse primer (SEQ ID NO: 4):
5'-ATAGCGGCCGCGCTCCTACTCGAGACAAACTCAGCAAATGC-3'
```

100 μl of the PCR reaction mixture was prepared by adding 250 μM dNTP, 20 pmol of each primer, 1.5 mM MgCl$_2$, 10 μl of a 10× buffer, 100 ng of a DNA template, and 1 unit of pfu polymerase, and PCR was performed as follows: initial denaturation at 95° C. for 5 minutes, then 25 cycles of denaturation at 95° C. for 1 minute, annealing at 55° C. for 30 seconds, and extension at 72° C. for 3 minutes. DNA fragments obtained by PCR were digested with NdeI/NotI restriction enzymes, purified on 1% agarose gel, and ligated into a pET21a plasmid digested with the same restriction enzymes to construct pET21a-Sde_BAga for each case.

Figure 4A:
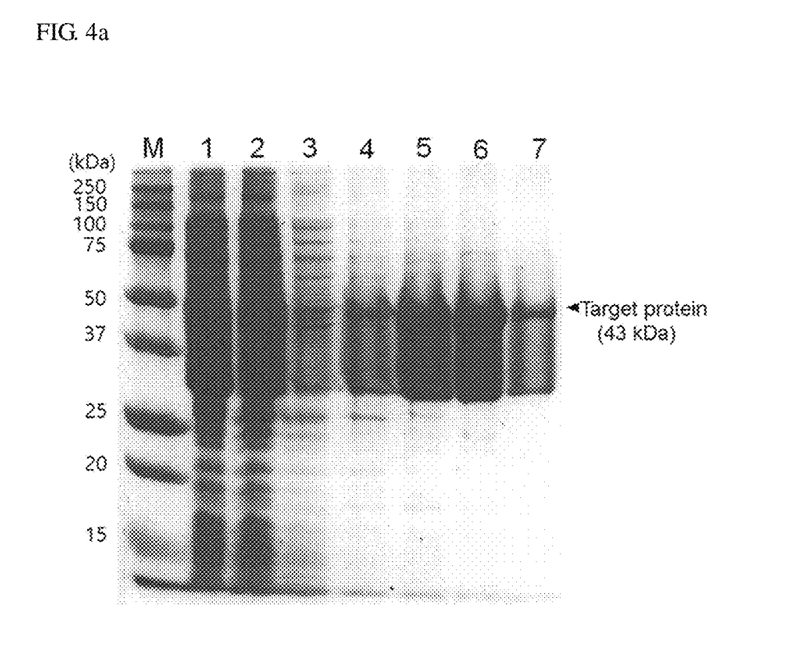
FIG. 4a illustrates SDS-PAGE analysis results of recombinant agarooligosaccharide hydrolase.

The constructed plasmids were introduced into *Escherichia coli* BL21 (DE3). To pre-culture the recombinant *E. coli* having the agarooligosaccharide hydrolase gene introduced therein, the cells were cultured in 10 mL of LB broth containing 100 μg/mL of ampicillin in a 50 mL-conical tube at 37° C. for 9 hours. Thereafter, 2 mL of the pre-cultured solution was inoculated into 100 mL of the present culture broth of the same medium composition, and then when the optical density value reached the mid-exponential phase (OD 0.4-0.6) using an optical density spectroscope, 0.1 mM isopropyl-beta-di-thiogalactopyranoside (IPTG) was added to allow induction at 30° C. for 16 hours. Then, the cell broth was centrifuged at 16,000×g for 20 minutes at 4° C., and then cells were recovered. The recovered cells were dispersed in 30 mL of a 20 mM Tris-HCl buffer (pH 7.4), and then the cells were lysed using a sonicator. Subsequently, the lysate was centrifuged at 16,000×g for 10 minutes at 4° C. to collect a supernatant. A recombinant enzyme included in the collected supernatant was purified using a Histrap column (5 mL, GE Health Care), and then the size of each purified protein was confirmed using an SDS-PAGE gel (see FIG. 4a). The salt (imidazole) used in protein purification was removed using a desalting column. The concentration of the recombinant protein enzyme from which the salt was removed was quantified using a BCA assay.

Example 3

Production of AHG by Agarooligosaccharide Hydrolase Reaction Using Agarobiose as Substrate 30.7 wt % (w/v) of agarose and agar was allowed to react under the conditions established in Example 1, i.e., 2% phosphoric acid and 110° C., 10 min (see Table 2). The amounts of both agarose and agar were based on a dry weight.

Agarooligosaccharide hydrolase reaction conditions are as follows. The acid hydrolysate obtained under the above conditions was neutralized to a pH of 5 to 6 using 5 M NaOH, and then a reaction was allowed to occur at 37° C. and 200 rpm for 12 hours.

The reaction product obtained after the enzymatic reaction was analyzed through thin layer chromatography (TLC) (see FIG. 4b) and GC/TOF-MS and HPLC (see FIG. 4c), and TLC, GC/TOF-MS, and HPLC analyses conditions were the same as those used in Example 1.

Figure 4B:
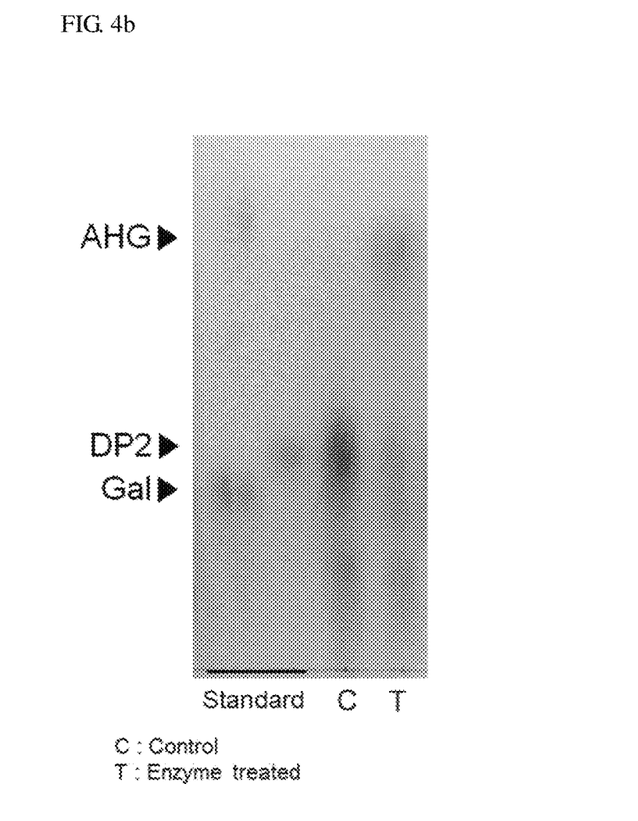
FIG. 4b is a TLC image showing a reaction product obtained by reacting agar or agarose having undergone acid treatment and neutralization with the agarooligosaccharide hydrolase.
Figure 4C:
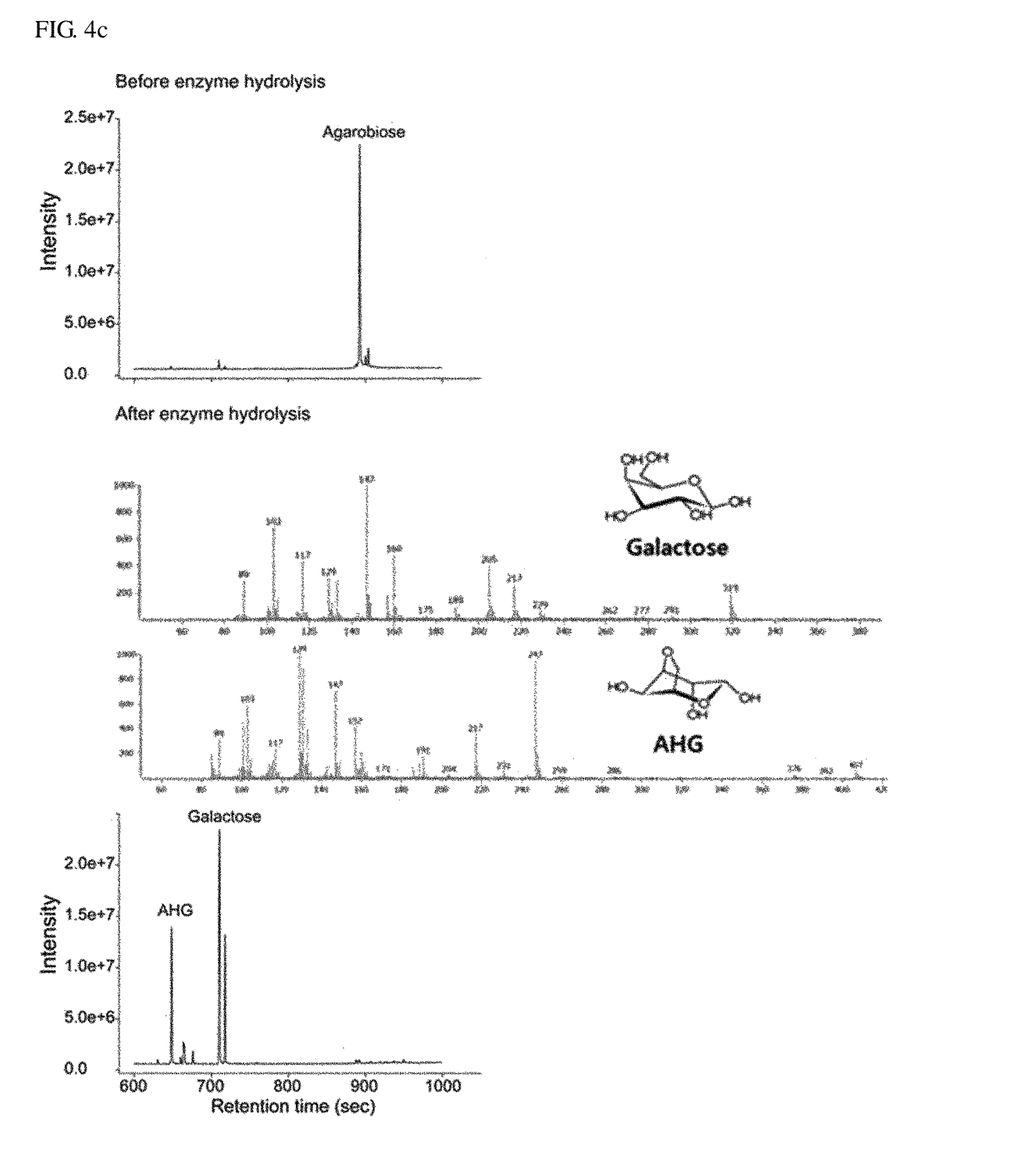
FIG. 4c illustrates GC-TOF/MS analysis results of a reaction product obtained by reacting agar or agarose having undergone acid treatment and neutralization with the agarooligosaccharide hydrolase.

As illustrated in FIGS. 4b and 4c, it was confirmed that agarobiose was converted into AHG and D-galactose by agarooligosaccharide hydrolase. At this time, the AHG yield obtained with respect to the amount (g) of agarose added was 43.3%.

Example 4

AHG Purification Using Yeast

The reaction products obtained in Example 3 were AHG and D-galactose, and yeast culture was performed in order to remove D-galactose. As a yeast strain, *Saccharomyces cerevisiae* D452-2 was used, and the strain was pre-cultured in YPD broth at 30° C. and 200 rpm for 24 hours. After culturing, the culture broth was centrifuged at 6,000×g for 10 minutes to obtain a cell pellet, the cell pellet was washed with a Tris-HCl buffer (pH 7.4), and then centrifuged once again under the same conditions to obtain a cell pellet.

Figure 5:
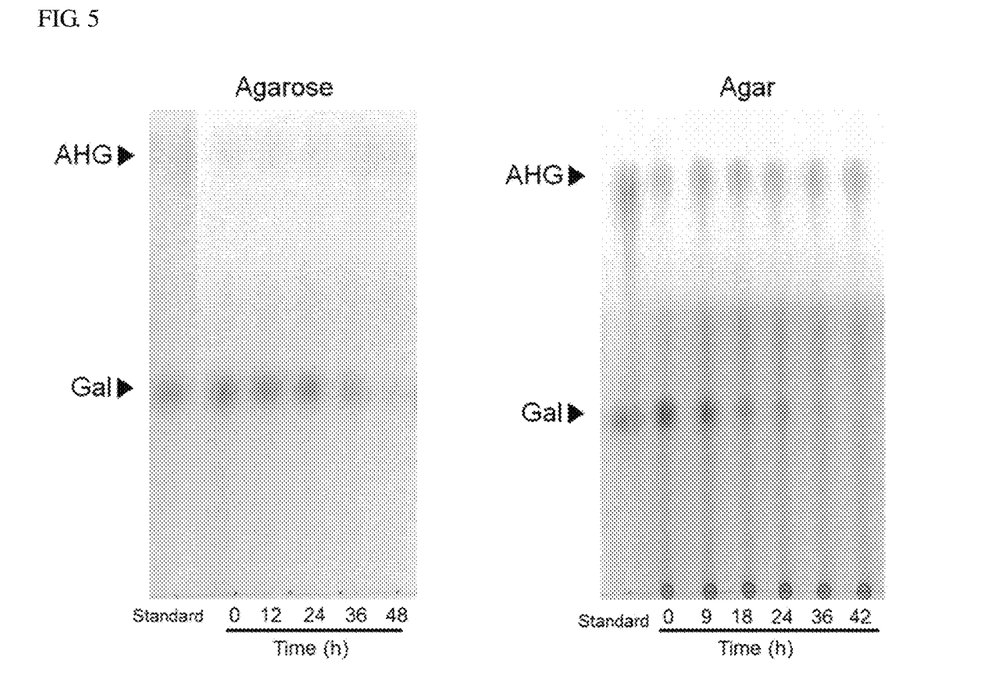
FIG. 5 is a set of TLC images showing results of confirming AHG purification using yeast, which is a GRAS microorganism, from agarose or agar, according to the AHG production process of the present invention, at different yeast culture time points.

For culturing, the cell pellet of *S. cerevisiae* D452-2 was inoculated into a minimal medium containing 3.35 g/L of a yeast nitrogen base and 0.4 g/L of CSM, using enzymatic reaction products, i.e., AHG and D-galactose, as carbon sources. The cell pellet was cultured at 30° C. and 200 rpm for 42 hours, and then TLC and GC-TOF/MS were performed, from which it was confirmed that D-galactose was completely consumed and only AHG remained (see FIG. 5), and the AHG yield was calculated as 33.2% (see Table 2).

TABLE 2

| Process | | Amount (g) Agarose | Amount (g) Agar | Yield (g product/100 g input substrate) Agarose | Yield (g product/100 g input substrate) Agar |
|---|---|---|---|---|---|
| supply | Initial substrate | 147.2 | 134.4 | NA* | NA |
| Acid hydrolysis | Agarobiose (DP2) | 132.6 | 83.8 | 90.1 | 62.4 |
| Treatment with agarooligosaccharide hydrolase | AHG/galactose | 63.4/70.5 | 29.2/32.9 | 43.3/47.9 | 21.8/24.5 |
| Yeast fermentation | AHG | 48.8 | 22.5 | 33.2 | 16.7 |

*not applicable

Example 5

Yield Comparison According to Existing Saccharification Processes

Monosaccharide yield and maximum substrate concentration in saccharification according to the present invention and conventional saccharification processes were compared. The results thereof are shown in Table 3 below.

TABLE 3

| Agarose saccharification methods | Acetic acid pretreatment and enzymatic saccharification using Aga50D, ABG, and NABH CH Lee et al. Process Biochem (2015) | Tris-HCl buffer pretreatment and enzymatic saccharification using Aga50D, ABG, and NABH CH Lee et al. Process Biochem (2015) | Enzymatic saccharification using Aga16B, Aga50D, and NABH | Present invention |
|---|---|---|---|---|
| Monosaccharide yield (% of theoretical maximum) | 50.5 | 44.9 | 72.5 | 62.6 |
| Maximum substrate concentration (w/v) | 15% | 5% | 1% | 30.7% |

As shown in Table 3, the maximum substrate concentration was significantly higher in the case of the present invention than in the existing processes.

Example 6

Establishment of Acid Hydrolysis Conditions of Agar

Hydrolysis was performed using 1% (w/v), 2% (w/v), or 3% (w/v) phosphoric acid at a reaction temperature of 90° C. for 480 minutes (8 hours), in the same manner as in Example 1, except that 20% (w/w) of agar was used as a substrate.

Figure 6:
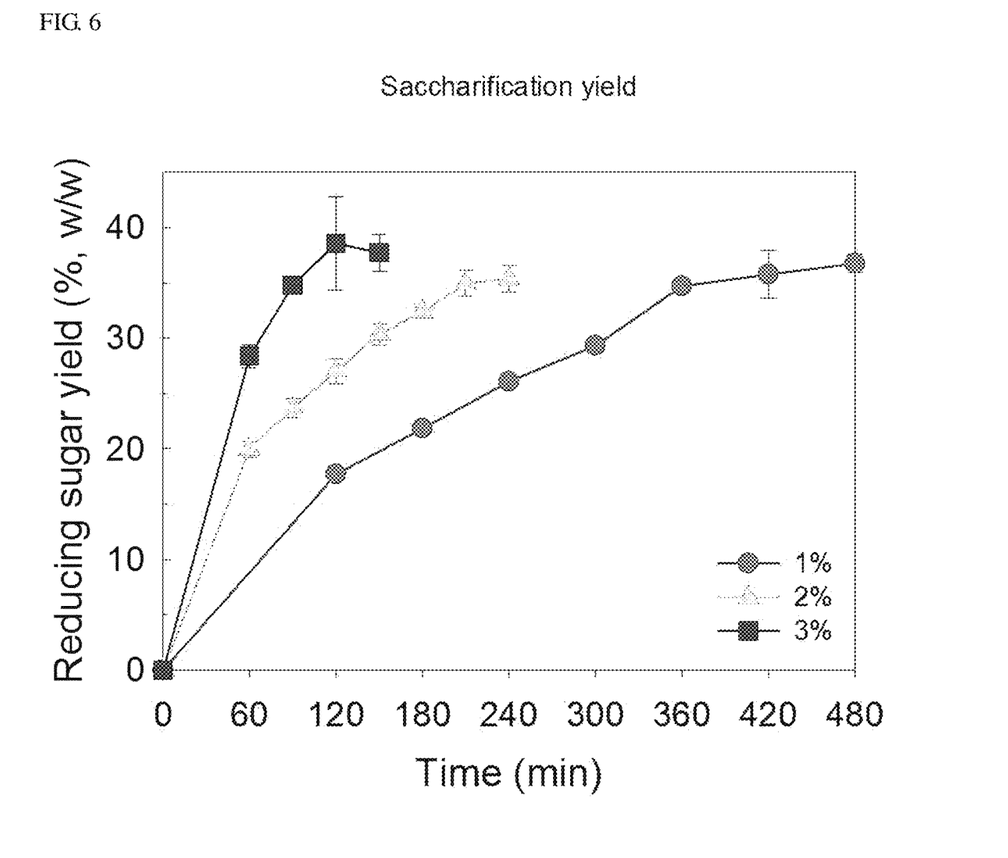
FIG. 6 illustrates the saccharification yield at different time points after acid hydrolysis of 20% (w/v) agar with phosphoric acid at a concentration of 1% (w/v), 2% (w/v), or 3% (w/v) at 90° C. according to the AHG production process of the present invention.

As illustrated in FIG. 6, the saccharification yield under each condition was increased over time.

To analyze the types of reaction products in accordance with the above conditions, HPLC analysis was performed in the same manner as in Example 1.

Figure 7A:
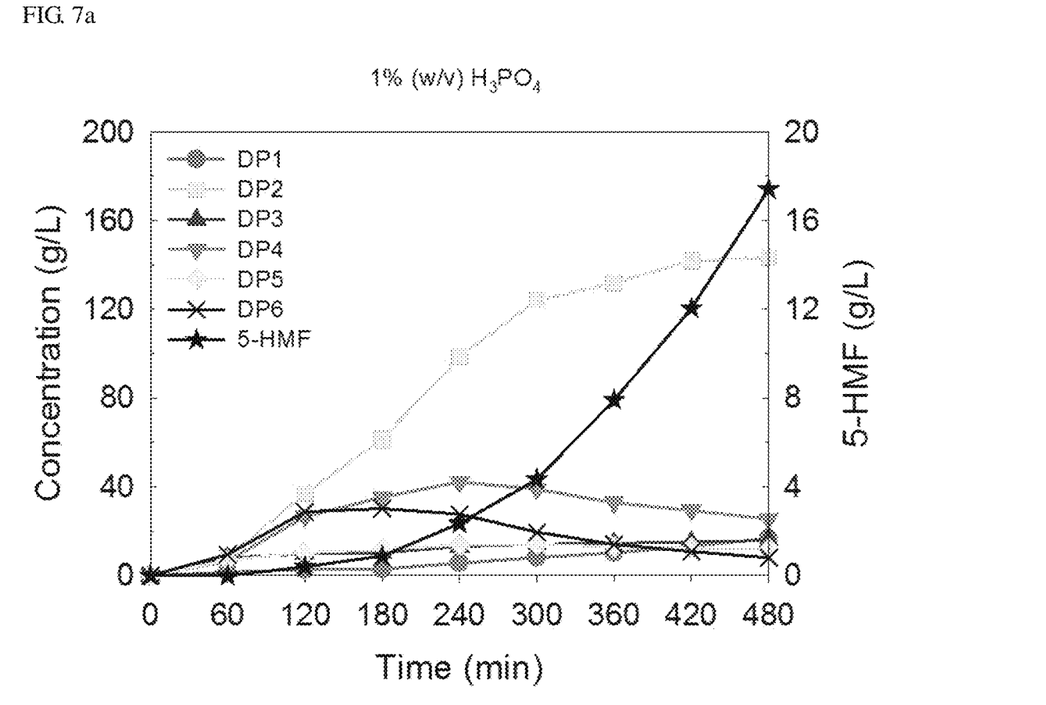
FIG. 7a illustrates HPLC analysis results of a reaction product obtained after treatment of agar with 1% (w/v) phosphoric acid and acid hydrolysis of the treated-agar at 90° C. for 480 minutes according to the AHG production process of the present invention.
Figure 7B:
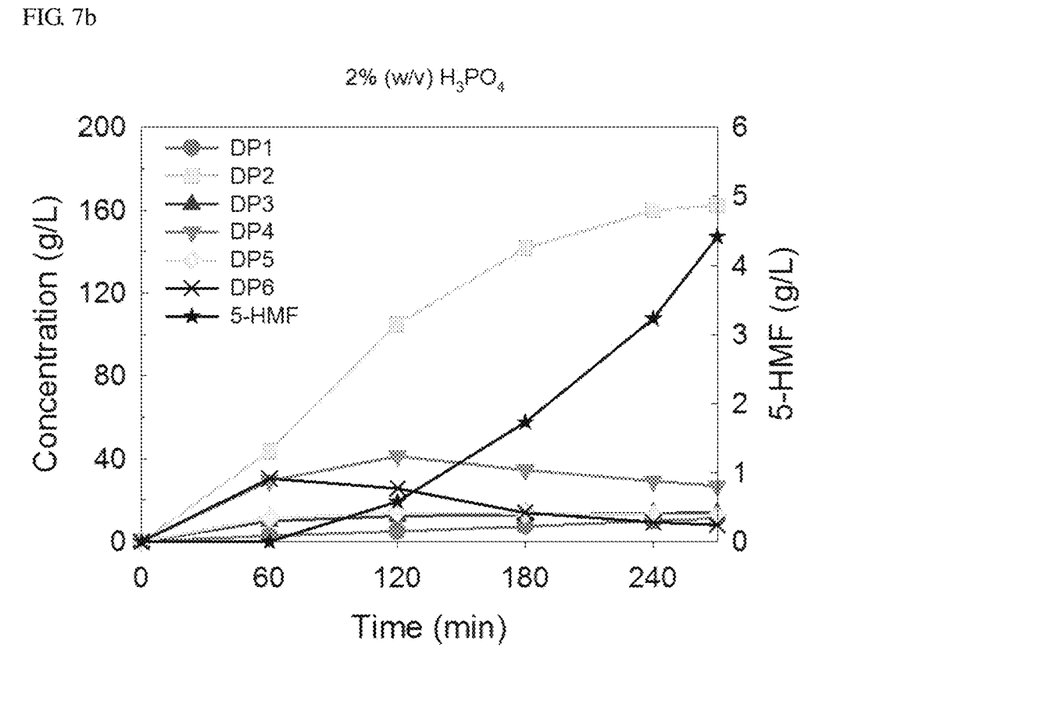
FIG. 7b illustrates HPLC analysis results of a reaction product obtained after treatment of agar with 2% (w/v) phosphoric acid and acid hydrolysis of the treated-agar at 90° C. for 480 minutes according to the AHG production process of the present invention.
Figure 7C:
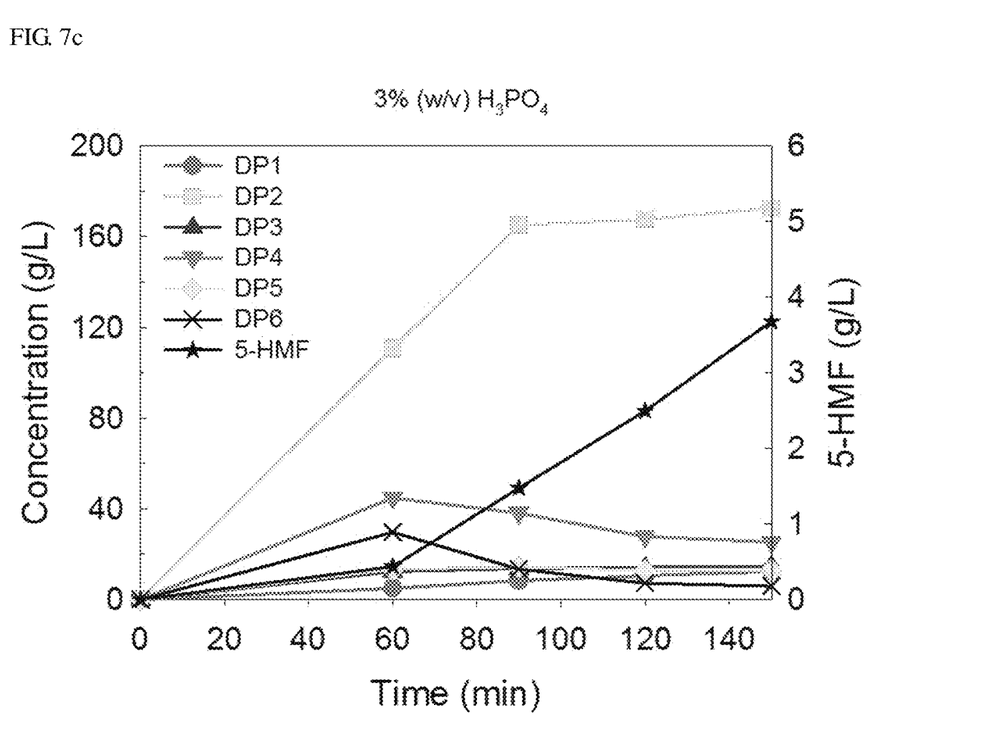
FIG. 7c illustrates HPLC analysis results of a reaction product obtained after treatment of agar with 3% (w/v) phosphoric acid and acid hydrolysis of the treated-agar at 90° C. for 480 minutes according to the AHG production process of the present invention.

As illustrated in FIGS. 7a, 7b and 7c, the concentration of agarobiose was 143.3 g/L under a condition of 1% phosphoric acid and 480 min, the concentration of agarobiose was 162.5 g/L under a condition of 2% phosphoric acid and 270 min, and the concentration of agarobiose was 172.7 g/L under a condition of 3% phosphoric acid and 150 min. These are yields corresponding to 64%, 73%, and 77%, respectively, with respect to the amount of added agar. The amount of 5-HMF as a by-product was very small, i.e., 4.4 g/L and 3.7 g/L under conditions of 2% phosphoric acid and 3% phosphoric acid, respectively. The method of the present invention is advantageous in that there is no need for an expensive high-pressure reactor since acid hydrolysis is performed at a relatively low temperature, and there is more safety at work.

The present invention can be used for the production of a high yield of 3,6-anhydro-L-galactose.

What is claimed is:

1. A method of improving a production yield of 3,6-anhydro-L-galactose comprising:
reacting agarose or agar in an amount of 10% (w/v) to 37% (w/v) with respect to a dry weight with a phosphoric acid at a concentration of 0.1% (w/v) to 5% (w/v) at 80° C. to 140° C. for 5 minutes to 500 minutes and then adding a strong base therein such that a pH of a reaction product comprising agarobiose is adjusted to 5 to 7, wherein a yield of 5-hydroxymethyl furfural in the reaction product is less than 1.5% (w/w) and the reaction product does not comprise agarotriose;
reacting the reaction product comprising agarobiose with agarooligosaccharide hydrolase sequences of SEQ ID NO: 1; and
culturing a microorganism having an ability to metabolize galactose in the presence of the hydrolysate obtained from the reaction of the agarooligosaccharide hydrolase and then centrifuging or filtrating the resulting microorganism culture broth to obtain 3,6-anhydro-L-galactose,
wherein the microorganism having an ability to metabolize galactose is any one of *Lactobacillus, Bifidobacterium, Bacillus, Streptomyces, Corynebacterium, Zymomonas, Escherichia coli,* and yeasts, and
wherein the method shows a higher production yield of 3,6-anhydro-L-galactose as compared to a control method where the agarooligosaccharide hydrolase sequence of SEQ ID NO: 1 has not been reacted with the reaction product agarobiose.

2. The method of claim 1, wherein the strong base comprises one or more selected from the group consisting of NaOH, KOH, Ca(OH)$_2$, and Ba(OH)$_2$.

3. The method of claim 1, wherein the reaction step between the reaction product and the agarooligosaccharide hydrolase is performed at a temperature ranging from 20° C. to 40° C. and 100 rpm to 300 rpm for 5 hours to 48 hours.

4. The method of claim 1, wherein the microorganism having an ability to metabolize galactose is cultured under an anaerobic condition.

* * * * *

SEQUENCE LISTING

<160> NUMBER OF SEQ ID NOS: 4

<210> SEQ ID NO 1
<211> LENGTH: 444
<212> TYPE: PRT
<213> ORGANISM: Saccharophagus degradans 2-40T

<400> SEQUENCE: 1

```
Met Asn Arg Leu Thr Leu Pro Pro Ser Ser Arg Leu Arg Ser Lys Glu
1               5                   10                  15

Phe Thr Phe Gly Val Ala Thr Ser Ser Tyr Gln Ile Glu Gly Gly Ile
            20                  25                  30

Asp Ser Arg Leu Pro Cys Asn Trp Asp Thr Phe Cys Glu Gln Pro Asn
        35                  40                  45

Thr Ile Ile Asp Asn Thr Asn Gly Ala Ile Ala Cys Asp His Ile Asn
    50                  55                  60

Arg Trp Gln Asp Asp Ile Glu Leu Ile Ala Asn Leu Gly Val Asp Ala
65                  70                  75                  80

Tyr Arg Phe Ser Ile Ala Trp Gly Arg Val Ile Asn Leu Asp Gly Ser
                85                  90                  95

Leu Asn Asn Glu Gly Val Thr Phe Tyr Lys Asn Ile Leu Thr Lys Leu
            100                 105                 110

Arg Glu Lys Asn Leu Lys Ala Tyr Ile Thr Leu Tyr His Trp Asp Leu
        115                 120                 125

Pro Gln His Leu Glu Asp Ala Gly Gly Trp Leu Asn Arg Asp Thr Ala
    130                 135                 140

Tyr Lys Phe Arg Asp Tyr Val Asn Leu Ile Thr Gln Ala Leu Asp Asp
145                 150                 155                 160

Asp Val Phe Cys Tyr Thr Thr Leu Asn Glu Pro Phe Cys Ser Ala Tyr
                165                 170                 175

Leu Gly Tyr Glu Ile Gly Val His Ala Pro Gly Ile Lys Asp Leu Ala
            180                 185                 190

Ser Gly Arg Lys Ala Ala His His Leu Leu Ala His Gly Leu Ala
        195                 200                 205

Met Gln Val Leu Arg Lys Asn Cys Pro Asn Ser Leu Ser Gly Ile Val
    210                 215                 220

Leu Asn Met Ser Pro Cys Tyr Ala Gly Ser Asn Ala Gln Ala Asp Ile
225                 230                 235                 240

Asp Ala Ala Lys Arg Ala Asp Asp Leu Leu Phe Gln Trp Tyr Ala Gln
                245                 250                 255

Pro Leu Leu Thr Gly Cys Tyr Pro Asp Ala Ile Asn Ser Leu Pro Asp
            260                 265                 270

Asn Ala Lys Pro Pro Ile Cys Glu Gly Asp Met Ala Leu Ile Ser Gln
        275                 280                 285

Pro Leu Asp Tyr Leu Gly Leu Asn Tyr Tyr Thr Arg Ala Val Phe Phe
    290                 295                 300

Ala Asp Gly Asn Gly Gly Phe Thr Glu Gln Val Pro Glu Gly Val Glu
305                 310                 315                 320

Leu Thr Asp Met Gly Trp Glu Val Tyr Pro Gln Gly Leu Thr Asp Leu
                325                 330                 335

Leu Ile Asp Leu Asn Gln Arg Tyr Thr Leu Pro Pro Leu Leu Ile Thr
            340                 345                 350

Glu Asn Gly Ala Ala Met Val Asp Glu Leu Val Asn Gly Glu Val Asn
        355                 360                 365
```

```
Asp Ile Ala Arg Ile Asn Tyr Phe Gln Thr His Leu Gln Ala Val His
    370                 375                 380

Asn Ala Ile Glu Gln Gly Val Asp Val Arg Gly Tyr Phe Ala Trp Ser
385                 390                 395                 400

Leu Met Asp Asn Phe Glu Trp Ala Leu Gly Tyr Ser Lys Arg Phe Gly
                405                 410                 415

Ile Thr Tyr Val Asp Tyr Gln Thr Gln Lys Arg Thr Leu Lys Ala Ser
            420                 425                 430

Gly His Ala Phe Ala Glu Phe Val Ser Ser Arg Ser
            435                 440

<210> SEQ ID NO 2
<211> LENGTH: 1335
<212> TYPE: DNA
<213> ORGANISM: Saccharophagus degradans 2-40T

<400> SEQUENCE: 2
```

| | | | | | |
|---|---|---|---|---|---|
| atgaatagac | ttacactacc | gccttcttct | cgtttgcgca | gcaaagagtt | tacctttggt | 60
| gttgcaacgt | cgtcttacca | aattgaaggc | ggcatagatt | ctcgcctgcc | ctgtaattgg | 120
| gatacgttct | gtgagcagcc | caataccatt | attgataaca | ccaacggcgc | cattgcttgc | 180
| gaccacataa | atagatggca | agacgatata | gaacttattg | ccaacctagg | ggtagatgcc | 240
| taccgctttt | ctattgcgtg | gggccgtgtt | attaatttag | acggcagcct | caataatgaa | 300
| ggcgttacat | tttacaaaaa | tatttttaact | aagcttcgcg | aaaagaattt | aaaagcttat | 360
| ataacgctat | accactggga | cttgccacaa | catttagaag | atgctggcgg | ctggcttaac | 420
| cgcgataccg | cctacaagtt | tcgcgactat | gtaaacctta | taccccaagc | gcttgatgac | 480
| gatgtatttt | gctacacaac | gttaaacgag | ccttttgca | gtgcctacct | tggctatgaa | 540
| attggtgtac | acgcaccggg | tataaaagac | ttagccagtg | ggcgcaaagc | cgcacaccat | 600
| ttattacttg | cccatggctt | agctatgcaa | gtgctgcgaa | aaaactgccc | caatagttta | 660
| agcggcatag | tgttaaacat | gagcccttgt | tacgccggca | gcaacgcaca | agcagatata | 720
| gatgcagcaa | aacgcgcgga | cgatttatta | tttcagtggt | atgcacaacc | gctacttact | 780
| ggctgctacc | ctgatgcaat | aaaacagcctg | ccagacaatg | ccaaaccacc | tatttgtgaa | 840
| ggcgacatgg | cgttaataag | ccaacccttta | gattatttag | ccttaactta | ctatacccgc | 900
| gcagtatttt | ttgccgacgg | taatggcggt | tttaccgaac | aagtacctga | gggtgtagag | 960
| ctaaccgata | tgggctggga | agtttacccg | caaggcttaa | ccgatttact | aatagaccta | 1020
| aaccaacgct | ataccctacc | cccgttactt | attaccgaaa | acggcgcagc | aatggtggac | 1080
| gaacttgtta | acggcgaagt | taacgatatt | gcccgaataa | attattttca | aacccattta | 1140
| caagcggtac | acaacgccat | tgaacaaggt | gttgatgtac | gcggttattt | tgcttggagc | 1200
| ctaatggata | atttttgagtg | ggcactgggt | tacagcaaac | gattcggtat | tacctatgta | 1260
| gattaccaaa | cacaaaagcg | aacgctaaaa | gccagcggcc | acgcatttgc | tgagtttgtc | 1320
| tcgagtagga | gctaa | | | | | 1335

```
<210> SEQ ID NO 3
<211> LENGTH: 39
<212> TYPE: DNA
<213> ORGANISM: Artificial Sequence
<220> FEATURE:
<223> OTHER INFORMATION: Forward primer for amplifying
      agarooligosaccharide hydrolase

<400> SEQUENCE: 3
```

```
atacatatga atagacttac actaccgcct tcttctcgt                              39
```

<210> SEQ ID NO 4
<211> LENGTH: 41
<212> TYPE: DNA
<213> ORGANISM: Artificial Sequence
<220> FEATURE:
<223> OTHER INFORMATION: Reverse primer for amplifying
      agarooligosaccharide hydrolase

<400> SEQUENCE: 4

```
atagcggccg cgctcctact cgagacaaac tcagcaaatg c                           41
```